(12) United States Patent
Monk et al.

(10) Patent No.: US 10,806,496 B2
(45) Date of Patent: Oct. 20, 2020

(54) PROXIMAL TIBIAL OSTEOTOMY SYSTEM

(71) Applicant: OXFORD UNIVERSITY INNOVATION LIMITED, Oxfordshire (GB)

(72) Inventors: Andrew Paul Monk, Berkshire (GB); Andrew Price, Oxforshire (GB); William Jackson, Oxfordshire (GB); Cameron Peter Brown, Oxfordshire (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 90 days.

(21) Appl. No.: 15/776,627

(22) PCT Filed: Nov. 16, 2016

(86) PCT No.: PCT/GB2016/053575
§ 371 (c)(1),
(2) Date: May 16, 2018

(87) PCT Pub. No.: WO2017/085479
PCT Pub. Date: May 26, 2017

(65) Prior Publication Data
US 2018/0344371 A1    Dec. 6, 2018

(30) Foreign Application Priority Data
Nov. 16, 2015 (GB) .................................. 1520176.7

(51) Int. Cl.
*A61B 17/80* (2006.01)
*A61F 2/30* (2006.01)
(Continued)

(52) U.S. Cl.
CPC ...... *A61B 17/8095* (2013.01); *A61B 17/8057* (2013.01); *A61B 17/8061* (2013.01);
(Continued)

(58) Field of Classification Search
CPC . A61F 2002/30266; A61F 2002/30736; A61B 17/8095; A61B 17/8057;
(Continued)

(56) References Cited

U.S. PATENT DOCUMENTS

| | | | |
|---|---|---|---|
| 5,938,664 A | 8/1999 | Winguist | |
| 6,086,593 A * | 7/2000 | Bonutti | A61B 17/8004 128/898 |

(Continued)

FOREIGN PATENT DOCUMENTS

| | | |
|---|---|---|
| CN | 201365971 | 12/2009 |
| CN | 202637085 | 1/2013 |

(Continued)

OTHER PUBLICATIONS

GB Search Report for corresponding GB Patent Application GB1520176.7 dated Apr. 5, 2016, 6 pages.
(Continued)

*Primary Examiner* — David W Bates
*Assistant Examiner* — Marcela I Shirsat
(74) *Attorney, Agent, or Firm* — Lee & Hayes, P.C.

(57) ABSTRACT

A support plate, for supporting the two parts of a tibia after a tibial osteotomy, is generally in the shape of a T with a stem having top and bottom ends and a cross piece extending across the top end of the stem. The support plate has a rear surface arranged to contact the tibia. The rear surface of the stem is convex in its central longitudinal plane over a first region of the plate, and the rear surface of the cross piece is concave in its transverse plane.

8 Claims, 6 Drawing Sheets

(51) Int. Cl.
  *A61B 17/15* (2006.01)
  *A61B 17/16* (2006.01)
(52) U.S. Cl.
  CPC .......... *A61B 17/152* (2013.01); *A61B 17/154* (2013.01); *A61B 17/157* (2013.01); *A61B 17/1675* (2013.01); *A61F 2002/30266* (2013.01); *A61F 2002/30736* (2013.01)
(58) Field of Classification Search
  CPC . A61B 17/8061; A61B 17/151; A61B 17/152; A61B 17/157; A61B 17/1675; A61B 17/154
  USPC .............................. 606/87; 623/16.11, 23.72
  See application file for complete search history.

(56) References Cited

U.S. PATENT DOCUMENTS

| | | | |
|---|---|---|---|
| D458,374 S | | 6/2002 | Bryant et al. |
| 9,861,404 B2 * | | 1/2018 | Reiley ................ A61B 17/8095 |
| 2005/0080421 A1 | | 4/2005 | Weaver et al. |
| 2005/0192578 A1 | | 9/2005 | Horst |
| 2008/0300637 A1 | | 12/2008 | Austin et al. |
| 2010/0030277 A1 | | 2/2010 | Haidukewych et al. |
| 2011/0213376 A1 * | | 9/2011 | Maxson ................ A61B 17/151 |
| | | | 606/88 |
| 2012/0215225 A1 | | 8/2012 | Philippon et al. |
| 2013/0211463 A1 * | | 8/2013 | Mizuno .............. A61B 17/8095 |
| | | | 606/291 |
| 2014/0039498 A1 | | 2/2014 | Chatain et al. |
| 2015/0305752 A1 * | | 10/2015 | Eash .................... A61B 17/151 |
| | | | 606/82 |

FOREIGN PATENT DOCUMENTS

| | | |
|---|---|---|
| CN | 104095676 | 10/2014 |
| EP | 2510893 | 10/2012 |
| EP | 2623057 | 8/2013 |
| FR | 2405062 | 5/1979 |
| FR | 2980967 | 4/2013 |
| WO | WO2005020831 | 3/2005 |
| WO | WO2012131246 | 10/2012 |
| WO | WO2015146866 | 10/2015 |
| WO | WO2015160021 | 10/2015 |

OTHER PUBLICATIONS

GB Search Report for corresponding GB Patent Application GB1520176.7 dated Sep. 1, 2016, 3 pages.
PCT Search Report for corresponding International Application No. PCT/GB2016/053575 dated Apr. 25, 2017, 6 pages.
PCT International Preliminary Report on Patentability from corresponding PCT International Application No. PCT/GB2016/053575 dated May 31, 2018, 10 pages.

* cited by examiner

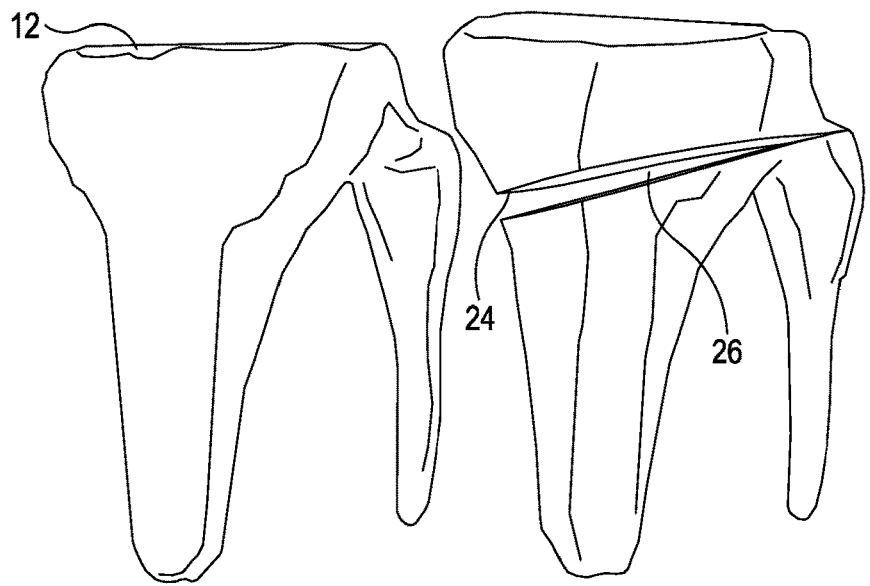
Fig. 3
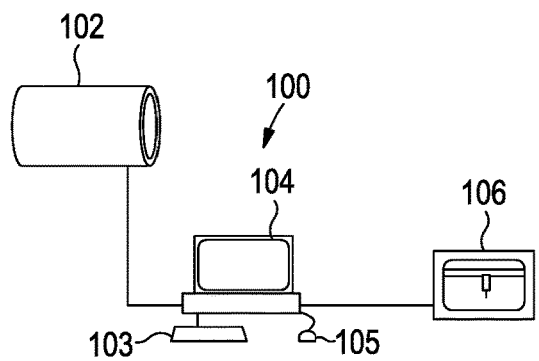
Fig. 4
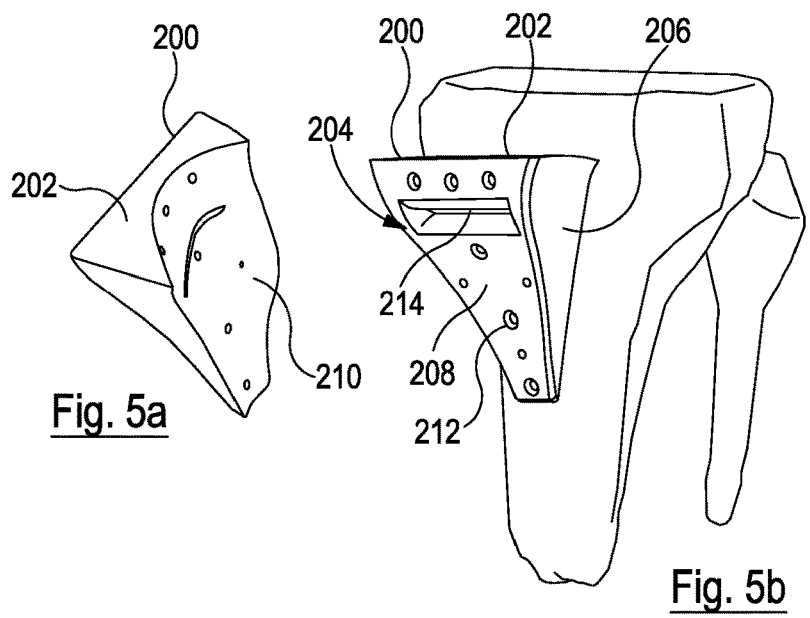
Fig. 5a
Fig. 5b

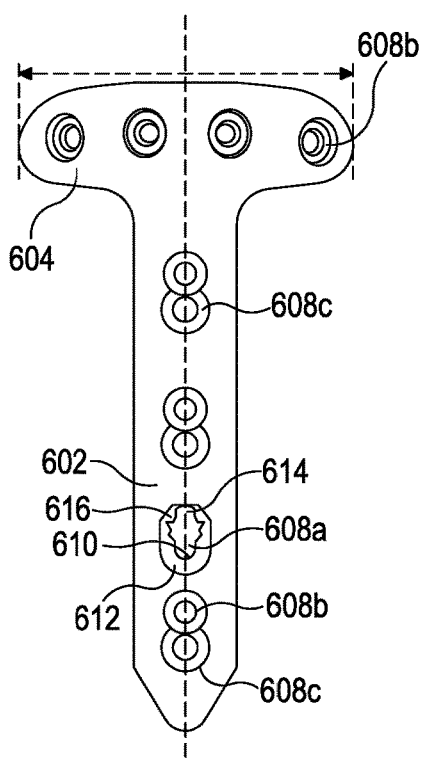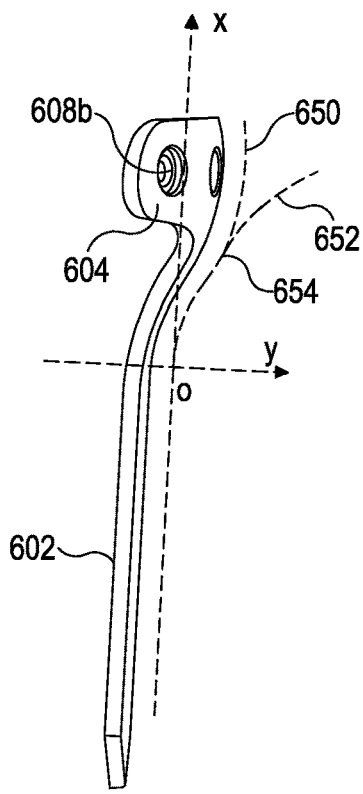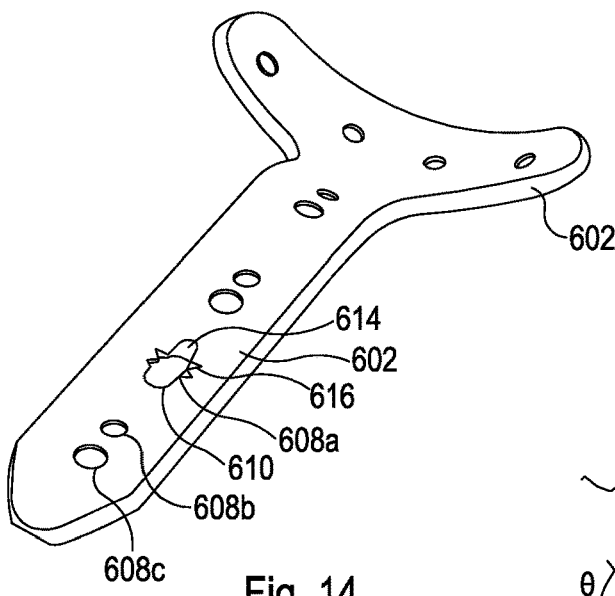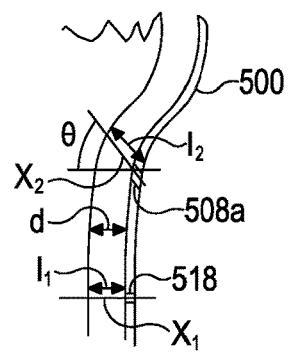
Fig. 12
Fig. 13
Fig. 14
Fig. 10a

PROXIMAL TIBIAL OSTEOTOMY SYSTEM

FIELD OF THE INVENTION

This present invention relates to bony osteotomy and in particular, but not exclusively, to high tibial osteotomy employing the creation of an opening wedge and fixation of the bone and wedge.

BACKGROUND TO THE INVENTION

The primary indication for high tibial osteotomy (HTO) is symptomatic, early medial compartment osteoarthritis in a varus knee (Flecher X, Parratte S, Aubaniac J M, et al. A 12-28-year followup study of closing wedge high tibial osteotomy. Clinical orthopaedics and related research 2006; 452:91-6 doi: 10.1097/01.blo.0000229362.12244.f6[published Online First: Epub Date]; Jackson J P, Waugh W, Green J P. High tibial osteotomy for osteoarthritis of the knee. The Journal of bone and joint surgery British volume 1969; 51(1):88-94). HTO is a particularly attractive option for physiologically young individuals as it permits high activity levels whilst maintaining a patient's native joint, thereby delaying the need for arthroplasty (Insall J N, Joseph D M, Msika C. High tibial osteotomy for *varus* gonarthrosis. A long-term follow-up study. The Journal of bone and joint surgery American volume 1984; 66(7):1040-8; Nagel A, Insall J N, Scuderi G R. Proximal tibial osteotomy. A subjective outcome study. The Journal of bone and joint surgery American volume 1996; 78(9):1353-8) which is associated with problems of wear and loosening in this cohort (Diduch D R, Insall J N, Scott W N, et al. Total knee replacement in young, active patients. Long-term follow-up and functional outcome. The Journal of bone and joint surgery American volume 1997; 79(4):575-82). Despite this, long-term studies have indicated that the clinical success of HTO deteriorates with time, with around half remaining effective after seven years. The reasons for subsequent lack of success are thought to relate to inaccuracies in technique based on issues including but not restricted to:

- a lack of knowledge surrounding the optimal corrected position (for example whether and how to neutralize stress in both compartments, offload the medial compartment completely, optimize for unicompartmental knee replacement (UKR), and select the degree of sagittal plane correction)
- poor instrumentation to deliver a surgical plan in a biomechanical environment which is intolerant of inaccuracy of +/−1 mm
- bulky plates causing irritation
- stiff plates not optimizing the strain environment for healing of the opened wedge
- an insufficiently patient-specific approach.

SUMMARY OF THE INVENTION

The present invention provides a support plate for supporting the two parts of a tibia after a tibial osteotomy. The support plate may be generally in the shape of a T. The support plate may comprise a stem having top and bottom ends. The support plate may comprise a cross piece, which may extend across the top end of the stem. The support plate may have a rear surface arranged to contact the tibia. The rear surface of the stem may be convex in its central longitudinal plane over a first region of the plate. The rear surface of the cross piece may be concave in its transverse plane.

The width of the cross piece, for example at its widest point, in the direction perpendicular to the length of the stem, may be in the range from 30 to 42 mm. For example it may be in the range from 33 to 40 mm.

The rear surface of the plate may be concave in the vertical plane in a second region of the plate which may be above the first region.

The rear surface of the stem may be substantially straight in the vertical plane over a lower region of the plate, which may be below the first region.

The rear surface of the stem may be concave in at least one horizontal plane.

The thickness of the plate may be substantially constant over the majority of its area.

The support plate may have screw holes therethrough arranged to receive screws for fixing the securing member to the upper and lower parts of the tibia.

One or more of the screw holes may be threaded, or arranged for threading engagement with the screws. One or more of the screw holes may be unthreaded.

One or more of the screw holes may be a multi-axis hole defining a plurality of screw axes along which a screw can be inserted through the hole into the tibia.

The invention further provides a support system for supporting the two parts of a tibia after a tibial osteotomy, the system comprising a support plate according to the invention and a plurality of screws for securing the support plate to the tibia.

One, or more, of the screws may have a differential pitch. For example they may have an upper shank and a lower shank, with the pitch of the threads on the upper shank being steeper than the pitch of the threads on the lower shank.

The present invention further provides a system for securing upper and lower parts of a tibia in a tibial osteotomy, the system comprising: a cutting guide having a rear surface arranged to match an area of the surface of the tibia and arranged to determine the position of a cut in the tibia which can divide the tibia into upper and lower parts and can be opened to form a gap; a wedge-shaped prosthesis for location in the gap between the upper and lower parts; and a securing member arranged to be located in a position relative to the tibia where it extends across the gap and having screw holes therethrough arranged to receive screws for fixing the securing member to the upper and lower parts, at least one of the screw holes defining a screw axis along which a screw passing through the screw hole will move into the tibia, wherein the screw axis is arranged to extend, when the prosthesis and the securing member are in position, through at least one of the upper and lower parts and the prosthesis.

The position of the securing member, in use, relative to the tibia, may be uniquely defined by a locating surface, or set of locating points, on the securing member, which are arranged to match the surface of the tibia only when the securing member is in a unique target position. Alternatively, or in addition, the position of the securing member, in use, may be defined by the cutting guide. For example the cutting guide The screw axis may be arranged to extend through one of the upper and lower parts, through the prosthesis, and into the other of the upper and lower parts.

The system may further comprise a screw arranged to extend through the securing member and one of the upper and lower parts, and into the prosthesis, and optionally into the other of the upper and lower parts.

The cutting guide may define a drill guide hole having a central axis which, when the cutting guide is in place, may be coincident with the position of the screw axis when the securing member is in place.

The present invention further provides a system for securing two parts of a bone in an osteotomy, the system comprising: a securing member which may be arranged to extend across a gap between the two parts, and may have screw holes therethrough arranged to receive screws for fixing the securing member to the parts. One of the screw holes may be threaded. The system may further comprise a screw having a shank comprising a lower portion arranged to be located in the bone and an upper portion arranged to engage in the threaded screw hole, wherein the upper portion has a thread which is different from, for example steeper than, that of the lower portion whereby, when the lower portion is engaged in the bone and the upper portion is engaged in the threaded hole, rotation of the screw to move the screw into the bone may result in movement of the securing member away from the bone.

A further one of the screw holes may also be threaded and the system may include a further screw also having a shank comprising a lower portion arranged to be located in the bone and an upper portion arranged to engage in the threaded screw hole, wherein the upper portion has a thread which is different from, for example steeper than, that of the lower portion.

One of the screw holes may be non-threaded and the system may comprises a further screw having a single constant pitch arranged to extend through the non-threaded hole to fix the securing member to the bone.

The invention further provides a method of performing an osteotomy comprising: forming a cut in a bone; opening the cut to form a gap and inserting a prosthesis into the gap; placing a securing member across the gap and fixing it to the bone on both sides of the gap, wherein fixing the securing member comprises inserting a screw through a screw hole in the securing member, through the bone on one side of the gap and into the prosthesis.

The method may further comprise inserting the screw through the prosthesis and into the bone on the other side of the gap.

The invention further provides a method of performing an osteotomy comprising forming a cut in a bone; opening the cut to form a gap; placing a securing member across the gap and fixing the securing member to the bone on both sides of the gap, wherein the securing member has a threaded screw hole therethrough, and fixing the securing member includes inserting a screw which has a shank having threaded upper and lower portions, the thread of the upper portion matching that of the threaded screw hole and being steeper than that of the lower portion whereby, as the screw is rotated to insert it into the bone, the securing member is lifted away from the surface of the bone.

The system or method may further comprise, in any workable combination, any one or more features of the preferred embodiments of the invention which will now be described by way of example only with reference to the accompanying drawings.

BRIEF DESCRIPTION OF THE DRAWINGS

FIG. 3 is a comparison of the proximal tibia of FIG. 2 before and after formation of an open wedge;
FIG. 4 is a schematic diagram of a system for imaging a knee and designing and producing components of a patient-specific system;
FIG. 5a is a perspective view of a cutting guide according to an embodiment of the invention;
FIG. 5b shows the cutting guide of FIG. 4a in use;
FIG. 10a shows how the angles of the screws in the plate of FIG. 10 affect the differential threading required on those screws;
FIG. 12 is a front view of a support plate according to a further embodiment of the invention;
FIG. 13 is a side view of the support plate of FIG. 12;
and
FIG. 14 is a perspective view of the support plate of FIG. 12.

DESCRIPTION OF THE PREFERRED EMBODIMENTS

Figure 1:
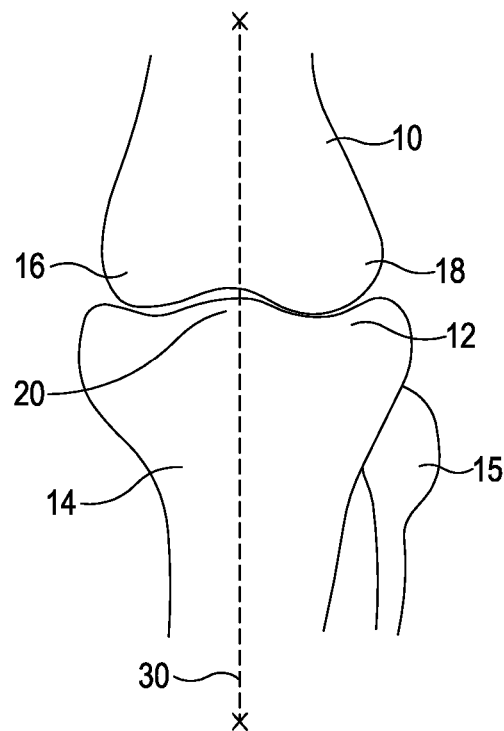
FIG. 1 is an anterior view of a left knee.

Referring to FIG. 1, the knee joint is where the distal end of the femur 10 rests on the tibial plateau 12 at the proximal end of the tibia 14. The upper end of the fibula 15 is below the tibial plateau 12. The medial and lateral condyles 16, 18 of the femur each bear on the superior surface of the tibial plateau. If the alignment between the femur 10 and tibia 14 is correct, the loading on the two condyles 16, 18 is approximately equal, and the direction of loading is vertically through the intercondylar eminence 20 in the centre of the tibial plateau 12, i.e. in the direction of the arrow 22 shown in FIG. 2. If the alignment of the knee moves away from the ideal, for example in a varus knee, the loading in the knee becomes uneven and various complications arise.

Referring to FIG. 3, one method of treatment of a varus knee is a high tibial osteotomy, in which the orientation of the top of the tibial plateau 12 is adjusted by making a cut 24 through the tibia 14 below the plateau 12, in this case from the medial side in the lateral direction and slightly upwards, and then opening the cut 24 to form a wedge shaped gap 26. The two parts of the tibia on either side of the cut can then be secured in place relative to each other, for example using a securing member such as a plate extending across the open end of the gap 26 and secured to the bone on either side, and optionally a wedge-shaped prosthesis located in the gap 26. It will be appreciated that osteotomy can be performed on other bones, such as in the hip, to address other problems, and that a tibial osteotomy is only one example.

Figure 2:
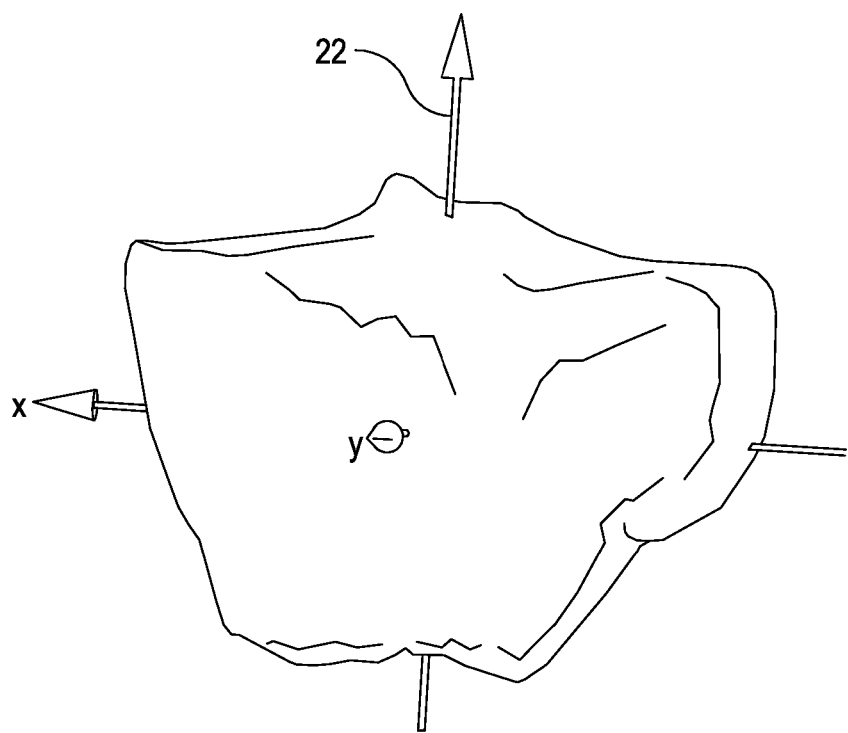
FIG. 2 is an anterior view of the proximal tibia showing desired loading.

It will be appreciated that the exact position, size and orientation of the gap 26 will determine the final orientation of the top of the tibial plateau 12, and hence the load distribution in the tibia and femur and the final orientation of the tibia relative to the femur. Therefore, referring to FIG. 4, in order to optimize the final loading, a system 100 for the production of patient-specific components may comprise a scanner 102 arranged to scan the knee and form an image of it, which may be a 3-dimensional image. The scanner may be and X-ray or MRI scanner and may be arranged to generate an image dataset, such as a Dicom data set, defining a 3D image of the knee. The system may further comprise a computer 104 or other appropriate processing device which comprises a data input, a memory for storing data, software including an image analysis and modelling application, and a processor for running the application. The modelling application may be a finite element analysis (FEA) application, such as Geomagic™ which is arranged to generate a model of the knee from the image data set and to calculate forces in the knee joint from the model. FIG. 2 shows a model of a tibia as generated by the system. The computer 104 may be arranged to receive the image data set, directly or indirectly, from the scanner and analyse it to determine the optimum adjustment of the tibial plateau. The system may further comprise a component production station 106 which in this embodiment is a 3D printer, but could take other forms.

In order to determine the optimum adjustment to the orientation of the tibial plateau, the image analysis and modelling software may define one or more models of the knee which may define various parameters of the knee, and define how the load distribution in the knee varies with variation in those parameters. The image analysis part of the software may then be arranged to determine the values of those parameters for the imaged knee from the image data set, and then to determine the load distribution in the knee, and how that load distribution would change as a result of changes in the orientation of the tibial plateau. From that data, and a target load distribution, it may be arranged to determine the optimum adjustment of the tibial plateau. Alternatively it may enable a user to input trial adjustments to the tibial plateau, via a user input, such as a keyboard 103 or mouse 105 associated with the computer 104, and determine the resulting load distribution for each trial adjustment, so that the user can then select an optimum adjustment. The parameters may include the relative positions of a number of points in the knee joint, and from the relative positions of those points such as the level of the lowest points on the medial and lateral condyles 16, 18 on the femur, for example measured in the direction along a central vertical axis of the femur, and the level of the lowest points on the tibial plateau 12, for example measured in the direction along a central axis of the tibia, as well as the relative orientations (e.g. the varus/valgus angle) of the tibia and femur, and positions (such as offsets in the coronal and sagittal plane) of the tibia and femur. Alternatively, or in addition, they may include the points of contact between the femur 10 and the tibia 14. The load distribution may be defined, for example, by the mean position and direction of the forces on the femur, or the position and direction of the net force on the femur, as illustrated by an arrow such as that 22 in FIG. 2, or as a mean force position and direction on each condyle.

Referring back to FIG. 1, it will be appreciated that the net force through the leg can be considered as a single vector between a point A at the top of the femur and a point B at the bottom of the tibia, along the line 30 in FIG. 1. If the varus/valgus angle is adjusted, i.e. the orientation of the tibial plateau is adjusted in the coronal plane, the point at which than net force passes through the tibial plateau will move laterally in the coronal plane. Similarly if the orientation of the tibial plateau is adjusted in the sagittal plane, then the position at which the net force extends through the tibial plateau will move in the sagittal plane.

Once the desired adjustment has been determined, the software may be arranged to determine the size, shape, and/or orientation of the wedge-shaped gap 26 that needs to be opened up in the tibia to achieve that adjustment, and from that, optionally also the size, location and orientation of the cut 24 that needs to be made in the tibia so that it can be opened up to form the correct gap 26. Typically the cut 24 may be defined by a plane in which the cut will be made. The cutting plane may be perpendicular to the coronal plane of the patient, and angled upwards from the medial border of the tibia to the lateral border of the tibia. The plane may pass through the medial border 34 to 45 mm below the plane of the tibial plateau, for example 40 mm below the tibial plateau. The cutting plane may pass through the lateral border of the tibia level with the superior part of the fibula head.

The plane of the tibial plateau may be defined, for example, by taking a set of points on the tibial plateau, excluding the intercondylar eminence 20, and finding the plane which is the best fit, for example a least squares best fit, to those points.

The imaging system may be arranged to image the exterior of the tibia in detail, and the image data set may therefore be arrange to include image data defining the shape of the exterior of the tibia. From this data, together with the required adjustment, the software may be arranged to generate a digital model of a cutting guide 200 to guide cutting of the bone, a removable shim 300 or a wedge prosthesis 400 for locating in the gap formed in the opened cut, and a securing member such as a plate 500 for securing across the gap to hold the two parts of the tibia in the desired relative positions. Examples of these components are shown in FIGS. 5, 6, 7 and 8a to 8d. Alternatively the guide may be standard and the prosthesis or shim and the plate may be produced in a range of sizes so that one of them can be selected 'off the shelf' once the optimum adjustment has been determined.

Referring to FIGS. 5a and 5b, the cutting guide 200 may comprise a block of plastics material such as a printed polymer-based scaffold material. It may be of a very generally rectangular cross section, with a flat top 202 and parallel sides 204, 206, but may be tapered towards the bottom so that the front 208 and side 204, 206 surfaces are generally triangular. The back surface 210 may be profiled to fit against the tibia and therefore be concave. A number of screw holes 212 and a cutting slot 214 may extend through the guide 200 from the front surface 208 to the back 210. The cutting slot 214 may be located towards the top of the guide 200 and may be generally horizontal in use, but optionally inclined upwards towards the back. The screw holes 212 may be used both to receive screws to secure the guide to the tibia, and also form drill guide holes to guide a drill if holes are needed for the screws that secure the plate 500 in place. The points where the screw holes exit the back of the guide 200 may therefore correspond to the locations of screw holes in the plate 500, with the exception that a spacing correction will be required to account for the fact that the two parts of the tibia will be moved apart after the holes are drilled to open up the cut. Therefore the drill guide holes 212 on one side of the cutting slot 214 may have a spacing relative to each other equal to the spacing of the corresponding holes in the plate 500, and the drill guide holes on the other side of the cutting slot may also have a spacing relative to each other equal to the spacing of the corresponding holes in the plate 500, but the two groups of drill guide holes may be closer to each other than the corresponding groups of screw holes in the plate 500. In this case there are three holes in a horizontal line 212 across the top of the guide above the slot 214, and three more in a vertical line below it. Parameters of the cutting guide that can be varied to match the patient, as well as the shape of the rear surface, may include the position and/or orientation of the cutting slot 214, the position and/or orientation of screw holes 212, and the size of the guide, for example its height and/or width and/or thickness.

The rear surface 210 of the cutting guide may be shaped to match a correspondingly sized area of the surface of the tibia. For example the whole of the rear surface 210 may be shaped to match such an area of the tibia, or a number of contact points on the rear surface 210 may be arranged so that all of them can simultaneously contact corresponding points on the tibia. In this way, the rear surface 210 can form a locating surface which can be used to locate the guide in a single target position relative to the tibia. In this case the guide 200 will, but means of the cutting slot 214 and screw holes 212, uniquely define the positions and orientations of the cut and the drill holes relative to the tibia.

Alternatively, rather than a patient-specific guide, a standard cutting guide can be used, which will not be described in detail, but which allows the surgeon to set the guide to the cutting angle he thinks is appropriate.

Figure 6:
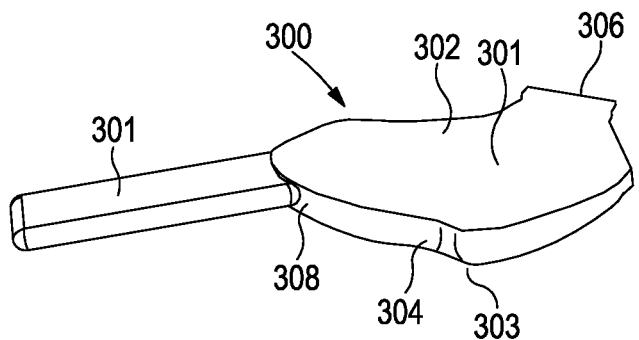
FIG. 6 is a perspective view of a removable shim for use in a method according to an embodiment of the invention.

Referring to FIG. 6, the removable shim 300 may be in the form of a thin wedge 302 and may have flat top and bottom surfaces 301, 303 and an outer peripheral surface 304 that is contoured to a shape corresponding to that of the tibia at the level where the cut 24 is to be made. At the rear edge 306 the edge of the shim 300 at its narrowest part may be straight where it may fit against the back of the cut 24. At the front edge 308, or at any other suitable location, a handle 310 may project from the main body of the wedge, so that it can be manipulated into position and removed. Since the shim 300 is not left in place, it is not essential for the outer surface 304 to match the shape of the tibia exactly, but if it does this helps the surgeon to locate the shim in the correct place relative to the tibia during use. Parameters of the shim 300 that can be varied according to the patient include the wedge angle in the coronal and/or sagittal plane, and the mean thickness of the wedge, i.e. the mean distance between the top and bottom surfaces 301, 303. Where a patient-specific shim is not produced for each patient, the shims can be produced as a range of sizes. For example they could be produced with coronal plane wedge angle ranging from 5° to 10° in 0.5° intervals, and the sagittal plane wedge angle being 1°, 2° or 3°, though other ranges and intervals are of course possible.

Figure 7:
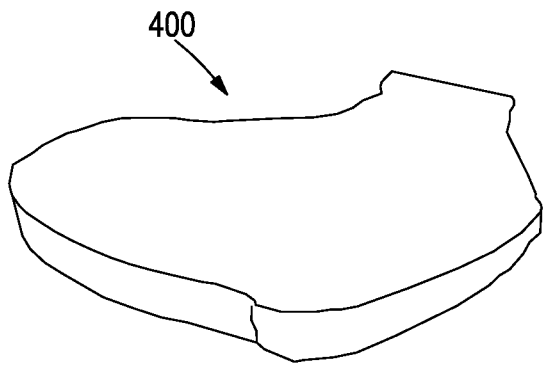
FIG. 7 is a perspective view of a patient-specific wedge according to an embodiment of the invention.

Referring to FIG. 7, the wedge prosthesis 400 may be the same shape, and with the same variable parameters, as the main body of the removable shim, with the handle 310 omitted. In this case, as the prosthesis is to remain in place, a good match between the shape of the outer surface of the prosthesis and the outer surface of the tibia is important.

Figure 8A:
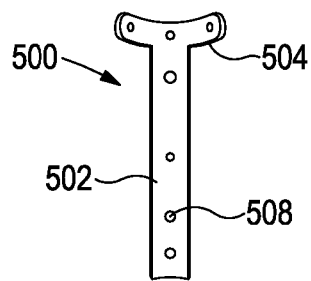
FIGS. 8a, 8b, 8c and 8d are views of a support plate according to an embodiment of the invention.
Figure 8B:
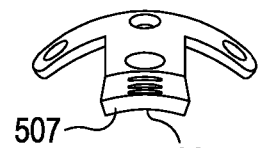
Figure 8C:
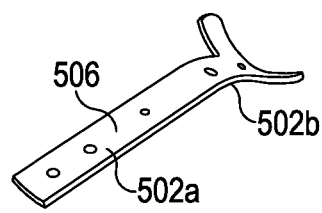
Figure 8D:
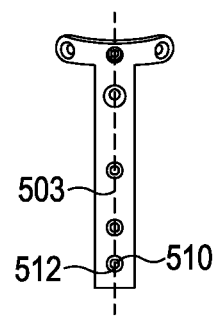
Figure 9:
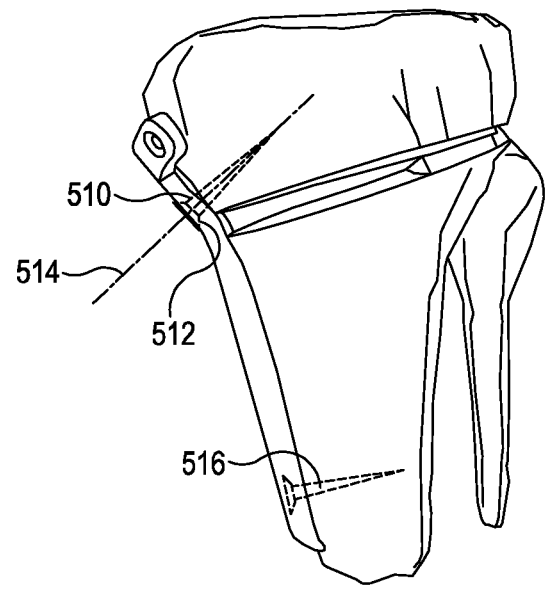
FIG. 9 shows the plate of FIGS. 8a-d in use without a wedge.

Referring to FIGS. 8a to 8d, the plate 500 may be generally of a T shape, but curved so as to fit closely against the surface of the tibia. It may therefore comprise a main portion or strip 502 which is generally vertical in use and forms a stem, and a cross piece 504 extending across the top of the main strip 502. The back surface 506 of the plate 500 which is arranged to fit against the tibia may be concave in at least some, or in all, horizontal planes (i.e. planes perpendicular to the length of the main strip 502 and perpendicular to the rear surface) to wrap around the tibia. This can be seen best in FIG. 8b where the bottom end 507 of the stem 502 in this embodiment is in a horizontal plane and corresponds in shape to the cross section of the stem 502 along the length of at least its lower portion. The rear surface of the plate 500 may be convex in the vertical plane (i.e. the plane parallel to the length of the main strip 501 and perpendicular to its rear surface), at least over a part of its length, which may be an intermediate region between its upper and lower ends, to follow the broadening of the tibia towards its upper end. The uppermost region of the plate 500, which may include the cross piece 504 and/or the region of the main strip just below it, may be concave in the central vertical plane of the plate. The central vertical plane referred to here is the plane of symmetry of the plate 500, which is the plane parallel to the length of the main strip 501 and perpendicular to its front and rear surfaces. In the embodiment of FIG. 8, this is the plane 503 perpendicular to the page in FIG. 8d. An intermediate region of the plate 500, below the uppermost region, may be convex in the vertical plane 503. The main strip 502 may have a substantially straight portion 502a at the lower end, furthest from the cross piece 504. The upper end closest to the cross piece 504 may have a single curved section 502b, or may have varying degrees of curvature along its length, for example with concave and convex portions of the rear surface as described above. A number of screw holes 508 are formed through the plate, in this case they correspond in relative positions to those in the cutting guide 200, and there may therefore be three in a line across the cross piece 504 and four in a line down the main strip 502. Each screw hole 508 may be made up of a main bore 510 of circular cross section and a countersink 512 having a common central longitudinal axis 514 which, referring to FIG. 9, may form a screw axis along which a screw can be inserted through the screw hole 508 into the tibia. In the simplest form the main bore 510 is unthreaded, and larger in diameter than the major diameter of the threaded shank of the screws, but it may be threaded, for example for use with a differentially threaded screw as will be described in more detail below. Parameters of the plate 500 that can be varied to fit the patient can include all of its dimensions and degrees of curvature, for example the curvature of the rear surface 506 of the main portion 502 in the direction transverse to its length (the transverse plane in use), i.e. as seen in FIG. 8b, the curvature of the rear surface of the cross piece 504 in the same direction, the curvature in the perpendicular direction (the coronal plane in use), the lengths of the main portion 502 and the cross piece 504, and the positions and orientations of each of the screw holes 508.

The thickness of the plate 500 may be substantially constant over the whole of its area, or it may taper towards the edges of the main portion 502 and/or the cross piece 504. For example its thickness, or mean thickness, may be less than half the width of the main portion 502, or less than a third of the width of the main portion. This gives the plate 500 a low profile, so that it fits closely to the bone which, together with the general T-shape of the plate which also minimizes its size, helps to reduce irritation of soft tissue around it.

Where a patient-specific plate is not produced for each patient, a range of plates can be produced so that they are available 'off the shelf', and these can have a range of dimensions, degrees of curvature, and thickness.

Figure 11:
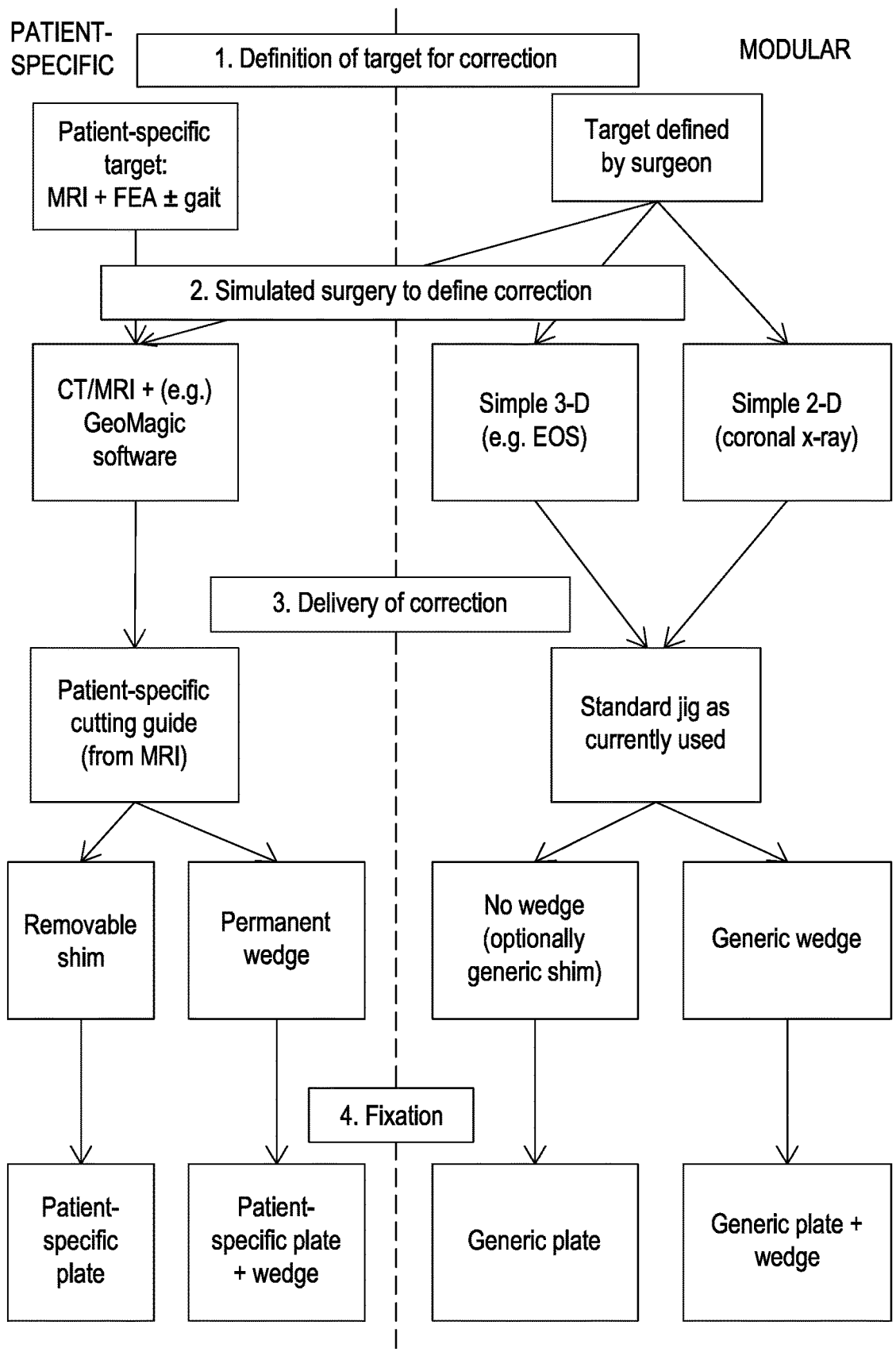
FIG. 11 is a flowchart showing a complete treatment process according to an embodiment of the invention.

Referring to FIG. 11, in use, the plate 500 can be of a generic design, or typically a group of generic designs of varying size and shape, which will be selected by the surgeon and used with standard imaging and cutting and with a generic wedge or shim, or with no wedge or shim. This process is outlined on the right hand side of FIG. 11. At stage 1 the surgeon determines the state of the knee, and then determines the correction that is needed to the orientation of the tibial plateau. The correction may be defined, for example, in terms of a single adjustment angle in the coronal plane, or adjustments in the coronal and sagittal planes.

These can be determined by the surgeon using 2D or 3D imaging, optionally with a degree of clinical examination to determine the coronal or sagittal adjustment. At stage 2 the surgery required to produce the target adjustment is determined using 3D imaging such as EOS imaging, or 2D imaging such as a coronal X-ray. At stage 3 the surgery is delivered to make the correction. A standard jig can be used to make the cut in the tibia, and either a generic wedge, or a generic removable shim may be used to support the two parts of the tibia in the desired relative positions. These may be selected from a set having varying coronal and sagittal adjustment angles. In some cases no wedge support may be needed. At stage 4, the fixation stage, either a generic plate is secured across the open gap in the tibia, or the generic wedge prosthesis is left in place in the gap and a generic plate is secured across the two parts of the tibia and the wedge.

Referring to the left hand side of FIG. 11, if a patient-specific set of components is to be use, a system such as that of FIG. 4 may be used. Firstly the knee may be imaged with an imaging system 102 which may be an MRI scanner, or an X-ray CT scanner. This may generate an image data set which can be used to generate an image of the femur and the tibia. The computer 104 may then be used to analyse the image data set to determine the optimum correction to the orientation of the tibial plateau. This may be done using 3D modelling software such as Geomagic™. This software can determine the forces that act between the femur and tibia in the knee as imaged, and in particular determine the direction and location (in the sagittal and coronal planes) of the net force between the tibia and femur. The software may then determine how those forces, or the net force, will change as a result of different corrections to the orientation of the tibial plateau. This allows the selection of an optimum correction, which can be defined for example as correction angles in the coronal and sagittal planes. The optimum correction angle may be defined in various ways. For example it may be selected so as to provide, as closely as possible within certain constraints, equal loads in the medial and lateral condyles. The constraints may include, for example, a maximum varus and/or valgus angle which could be 12°. The constraints may include limits on the position of the net force within the tibial plateau, for example they may include a range of positions on the tibial plateau. The range may be defined as a range of positions in the coronal plane, i.e. in the lateral direction, for example between 45% and 70% of the distance from the medial extremity of the tibial plateau to the lateral extremity of the tibial plateau. Alternatively, or in addition, the range may be defined as a range of positions in the sagittal plane, i.e. in the anterior/posterior direction between the anterior and posterior extremities of the tibial plateau.

The mean or net force through the knee may be determined not just by image analysis, but also by gait analysis. For example, prior to the surgery, the patient may be put through a gait analysis sequence in which forces in the leg are measured as the patient walks, and a kinetic data set recording the forces in the knee, and a kinematic data set recording the cycle of relative movement of the femur and tibia, are both recorded. Gait analysis systems are well known and will not be described in detail, but may include pressure sensitive plates that measure the distribution of forces across the sole of the foot as the patient walks, from which the net force through the tibia can be determined. This data can be analyzed in a number of ways, but may, for example, be used to provide a more accurate estimate of the net force through the knee, or the mean or time average of the net force over the course of the gait cycle. This can be used as described above to determine the optimum correction to the orientation of the tibial plateau. Alternatively a more complex FEA method may be used to calculate the pressure over the whole of the tibial plateau, or the mean (time averaged) pressure at each point over the gait cycle, and then the optimum wedge opening orientation and angle may be determined so as to provide the most even spread of pressure over the whole of the tibial plateau, or the most equal balance of net forces between the lateral and medial condyles. The forces and pressures may be used to determine the stress in the cartilage and or meniscus in the knee, and the wedge opening angle and direction calculated so as to optimize the stress. For example it may be chosen to minimize the stress in the medial condyle while maintaining the stress in the lateral condyle below a predetermined threshold. In any optimization a threshold maximum wedge angle may be defined, and the optimization carried out within the range of wedge angles below that threshold.

The software may then be arranged, from the target correction and the image data set, to select an optimum cutting plane, through the tibia, in which the cut is to be made, and optionally also the optimum cutting direction and cutting distance into the bone which will allow the cut to be opened up to leave a wedge shaped gap of correct size, shape and orientation to provide the target adjustment. For example this may be beginning at a point 40 mm below the joint line on the medial side, with the cutting plane passing out just above the fibula head on the lateral side. The cutting plane may be perpendicular to the coronal plane. From this data it may then be arranged to define the shape of a cutting guide 200, removable shim 300 or wedge 400, and plate 500.

The shape of the shim 300 (apart from the handle which is standard) or wedge 400 can be fully defined by the position and shape of the optimum gap 26 and the shape of the tibia in the plane of the cut 24.

The shape of the plate 500 may be chosen so that, when it is in position, i.e. in a position which can be determined by the software, it extends a sufficient distance either side of the gap 26 and has a sufficient number of screw holes to secure the bone in place, and the curvature of the back surface may be designed to fit closely against the bone when it is in that position. The positions and screw axis orientations of the screw holes 508 may be chosen so that the plate can be well secured to the bone. Other parameters of the plate 500 which can be selected include curvature of the back surface 506 of the main vertical strip 502, The shape of the cutting guide 200 may be designed so that its rear surface 210 fits closely to the surface of the tibia over an area that includes the front edge of the cut 24 and the points at which the screws will enter the bone, as determined by the positions of the screw holes 508 in the plate 500. The orientation and position of the set of drilling guide holes 212 may be arranged to correspond to the screw axes of the screw holes 508 in the plate 500, but adjusted to take account of the movement that will occur between the two parts of the tibia when the cut 24 is opened up to form the gap 26. It will be appreciated that, since the guide is located relative to the surface of the tibia by the shape of its rear surface, and the drilling guide holes 212 in the guide 200 and the screw holes 508 in the plate correspond with each other, the final 'in use' position of the plate relative to the tibia is also defined by the cutting guide 200 and, after the holes have been drilled, by the positions of the drilled holes in the tibia.

Once the shape of the components had been defined by the software, the computer may be arranged to control the 3D printer 106 to produce all of the required components. Then the surgeon can perform the operation, firstly by placing the cutting guide 200 in the correct location on the tibia, as shown in FIG. 5b, which is easy to identify due to the match between the rear surface of the guide 200 and the correct area of the tibia. The guide can then be secured in place for example by inserting screws through two or more of the drilling guide holes 212 into the tibia. With the guide 200 secured in place, the cut 24 in the tibia may be made using the slot 214 as a guide, and holes may be drilled in the tibia to receive the fixing screws using the guide holes 212. Then the guide 200 may be removed, the cut 24 opened up and the wedge prosthesis (when one is being used) inserted into the gap 26. Because the outer edge of the prosthesis 400 matches the shape of the tibia the correct location can easily be found. The plate 500 may then be secured to the bone, for example using screws 516 inserted through the holes 508 in the plate and screwed into the holes in the bone which may have been drilled using the guide 200.

Figure 10:
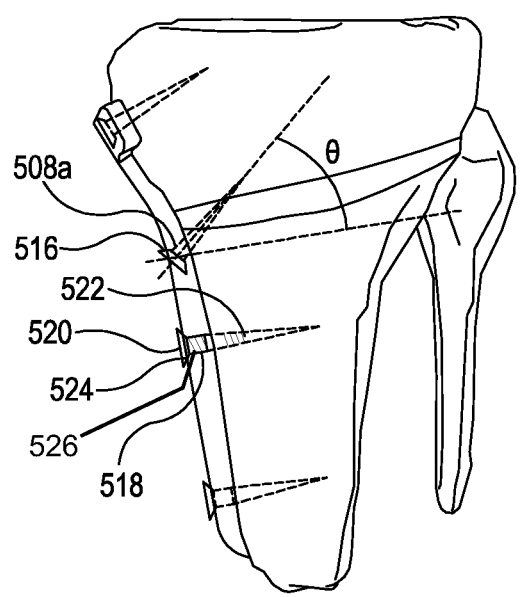
FIG. 10 shows the plate of FIGS. 8a-d in use with a wedge.

Referring to FIG. 10, one of the screw holes 508a in the plate may be located close to the plane of the cut 24, and may be angled such that the screw axis, and hence the screw 516 that is used with it, passes through the bone on one side of the gap 26, through the wedge prosthesis 400 and optionally through into bone on the other side of the gap 26. This means that, when the screw 516 is tightened it can further secure the two parts of the tibia and the wedge prosthesis 400 in place. For example, some or all of the screw holes in the main strip or stem 502 of the plate may lie in the central plane of symmetry 503 of the main strip 502, and the axis of the screw hole 508a may be at an angle θ to the direction normal to the rear surface of the plate 500 on the central plane of symmetry 503, which may also be at an angle θ to the axes of the other screw holes 518 in the straight lower portion of the main strip or stem 502. Those other screw holes 518 may have central axes that are normal to the rear surface of the plate 500. This angle θ may be in the range 30° to 58°, and may be in the range 40° to 52°. In this embodiment it is 46°.

Also referring to FIG. 10, some of the screw holes 518 in the plate 500 may be threaded and the screws 520 used in those holes may be differentially pitched. Specifically the screws 520 for use in the threaded holes 518 may have a lower shank 522, furthest from the head 524, having a first pitch, and an upper shank 526 which is of a second pitch. The second pitch may be steeper than the first pitch and match the pitch of the screw hole 518. The lower shank 522 may be narrower than the upper shank 526 so that it can pass freely through the screw hole 518 as the screw 520 is screwed into the bone with the plate held against the bone by the surgeon. Then when the upper shank 526 reaches the threaded screw hole 518, because of the differential thread, the screw may start to pass through the plate 500 more quickly than it passes into the bone, so the plate will be lifted off the surface of the bone. This may continue until the head of the screw 520 reaches the plate 500 which will stop further tightening of the screw.

Typically the system might include two differentially threaded screws which would be inserted first to locate the plate 500 in a slightly raised position, and then the rest of the screws would be standard cortical screws which would further secure the plate 500 in place. In other embodiments, rather than the screw hole 518 being threaded, it may be of a slightly narrower diameter than the major diameter of the upper shank 526 of the screw, and of a material such that the upper shank 526 of the screw can self-tap into the plate, and thereby threadingly engage with the screw hole 518 as if it were threaded.

Where one of the screw holes 508a is at an angle θ to the other screw holes 518, as described above, and that screw hole 508a and the other screw holes 518 are threaded for use with differentially threaded screws 516, 520, it will be appreciated that the differential threading of the screws 516, 520 will need to be different to achieve the same spacing between the plate 500 and the bone at the position of both screws. Referring to FIG. 10a, the distance l by which the plate 500 will be lifted away from the bone during tightening of a differential screw depends on the ratio of the pitch angles of the upper and lower shank, and the distance over which the screw will be screwed into the bone. If the screw axis is perpendicular to the surfaces of the bone and the plate, as for the screw hole 518, then those parameters will completely define the final spacing d between the plate and the bone, which will be equal to the lift distance $l_1$. However, for the screw hole 508a, the movement of the plate 500 during tightening of the screw is at an angle θ to the normal to the bone surface and so the final spacing d will be less than the lift distance $l_2$. Therefore to achieve a constant spacing d along the length of the plate 500, the lift distance $l_2$ produced by tightening the angled screw 516 needs to be greater than that of the screws 520 in the straight part of the plate 500. This may be achieved in a number of ways. The ratio of the pitch angles of the upper and lower shanks of the angled screw 516 may be greater than that of the other screws 520, or the length of the angles screw 516 may be greater than that of the others 520 so that it is screwed further into the bone than the other screws 520 which will result in a greater lift for the same pitch ratio, or a combination of screw length and pitch ratio can be used to achieve the necessary lift distance $l_2$.

It will also be noted that, for screw holes 518 that have a central axis normal to the rear surface of the plate, the direction of the lift caused by the differential thread is also normal to that surface. Therefore where there are two or three such holes, the screws in them can be tightened in any order. However, for the screw hole 508a that is angled to the others 518, the direction of lift is angled to the normal to the rear surface of the plate, and therefore tightening of the screw will result in a shift in the position of the plate 500, from its initial position in contact with the bone, in the direction along the length of the stem, i.e. generally in the direction of the distal end of the plate.

To compensate for this, the position and orientation of the drill holes in the bone need to be defined by, i.e. to have central axes that coincide with, the projection, of the central axes of the screw holes 508a, 518 in the plate, onto the bone, with the plate 500 in its intended final position spaced from the bone by the distance d. Referring back to FIG. 5b, the drill guide holes 212 in the cutting guide also need to be positioned so as to achieve the necessary drilling positions in the bone. The central axes of the drill guide holes 212, when the guide is in contact with the bone, therefore need to coincide with the central axes $X_1 X_2$ of the screw holes 518 508a, in the plate 500 when the plate 500 is in its intended final position as shown in FIG. 10a.

During tightening of the screws, the plate is first placed in contact with the bone, and the angled screw 516 is tightened first. This lifts the plate away from the bone by the spacing distance d and shifts it in the distal direction. A second screw 520 in the straight part of the plate 500 is then tightened which produces no lateral shift, but produces the same spacing distance d from the bone in the region of the second screw 520. The remaining screws may have constant thread pitch, i.e. not differential threading, and may therefore be tightened in turn, in their threaded screw holes in the plate, to further secure the plate at the same spacing d from the bone.

Referring to FIGS. 12 to 14, a support plate according to a further embodiment of the invention is similar to that of FIGS. 8a to 8d. Corresponding parts are indicated by the same reference numerals increased by 100, and only the differences will be described. There may be two groups of screw holes 608, one group 608b being threaded and one group 608c being non-threaded. There may be sufficient threaded screw holes 608b for the plate 600 to be secured entirely using those. Some, or all, of the threaded screw holes 608b may have respective non-threaded screw holes close to them so that one or more of the non-threaded screw holes 608c can be used instead of the threaded ones. One of the screw holes may be a multi-axis screw hole 608a. This may be defined by a number of surfaces. One of the surfaces 610 may be part cylindrical defining a first central axis and another of the surfaces 614 may also be part cylindrical and define a second central axis inclined to the first central axis. Each of these part cylindrical surfaces 610, 614 may be arranged to fit around the shank of a screw so that the screw may be inserted through the hole 608a in one of two directions along one of the two central axes. Two further surfaces 612, 616 may partially define respective countersinks, each aligned with a respective one of the part cylindrical surfaces 610a, 614a, and thereby arranged to receive the head of a screw inserted along one of the respective central axes.

Referring to FIG. 12, the width w of the cross piece 604, measured in a straight line in a direction perpendicular to the centre line of the stem 602, may be in range from 33 to 40 mm. For example it may be in the range from 30 to 42 mm. In this embodiment it is 36 mm.

Referring to FIG. 13, the profile of the rear surface 606 of the plate is also carefully designed. The profile is shown by the dotted line 650 in FIG. 13 which corresponds in shape to the centre line of the rear face 606. The lower, or distal, part 602a of the stem is straight. The upper, or proximal, part 602b of the stem is curved. The upper end of the distal part 602a and the lower end of the proximal 602b part can be considered as the point where the stem starts to curve. The shape of the curved proximal part can be defined as a function using a coordinate system as shown on FIG. 13 in which one axis, the x axis is in the direction parallel to the centre line of the straight distal part of the stem, with values of x increasing in the upward direction towards the proximal end of the plate, and the other axis, the y axis, in the perpendicular direction in the plane of symmetry of the plate, i.e. perpendicular to the back surface 606 on the centre line of the stem 602, with values of y increasing in the direction in which the convex front face 607 faces. The profile of the of the rear face 606 may therefore be defined by the function:

$$y=ax^b$$

where a is in the range 0.009 to 0.01, and may be in the range 0.0093 to 0.0094, and in this embodiment is 0.00936, and b is in the range 1.8 to 2.1, and may be in the range 1.85 to 2.0, and in this embodiment is 1.92.

This curved profile may continue over the whole of the upper part 602b of the plate as indicated by the curve 652. This upper part 602b may be in the range 40 to 50 mm long, and may be in the range from 44 to 46 mm long. For example it may be 45 mm long. Alternatively this curved profile may extend from the top of the lower straight part 602a upwards to a point of inflexion 654, where the direction of curvature reverses, and the back surface 606 (along the x axis as defined) ceases to be convex and becomes concave. The point of inflexion 654 may be 25 to 35 mm above the top of the straight lower part 602a, for example 30 mm above the top of the straight lower part. This is as illustrated by the curve 650 in FIG. 13, and as shown for the plate 600.

It will be appreciated that the various features of the various embodiments described above may be combined together in other combinations in still further embodiments of the invention, with the only limit on the possible combinations being the practicality of such combinations which will be readily understood by the skilled man.

The invention claimed is:

1. A system for securing upper and lower parts of a tibia in a tibial osteotomy, the system comprising a cutting guide having a rear surface arranged to match an area of the surface of the tibia and arranged to determine the position of a cut in the tibia which can divide the tibia into upper and lower parts and can be opened to form a gap, a wedge-shaped prosthesis for location in the gap between the upper and lower parts, a securing member arranged to be located in a position relative to the tibia where it extends across the gap and having screw holes therethrough arranged to receive screws for fixing the securing member to the upper and lower parts, and a screw, at least one of the screw holes defining a screw axis along which the screw is configured to pass through the screw hole to move into the tibia, wherein the screw axis and the screw are each arranged to extend, when the prosthesis and the securing member are in position, through the prosthesis and at least one of the upper and lower parts.

2. A system according to claim 1 wherein the screw axis and the screw are arranged to extend through one of the upper and lower parts, through the prosthesis, and into the other of the upper and lower parts.

3. A system according to claim 1 wherein the cutting guide defines one or more drill guide holes each having a central axis which, when the cutting guide is in place, is coincident with the position of the screw axis of one of the screw holes when the securing member is in place.

4. A system according to claim 3 wherein the securing member is defined as in place when it is configured to be spaced from the bone by a spacing distance.

5. A system according to claim 1 wherein the securing member has screw holes therethrough arranged to receive screws for fixing the securing member to the upper and lower parts wherein two of the screw holes each have a central axis and the central axis are non-parallel to each other, wherein each of said two screw holes is threaded, the system further comprising two screws, one for location in each of said two screw holes, each of the screws having a shank comprising a lower portion arranged to be located in the bone and an upper portion arranged to engage in the respective threaded screw hole, wherein the upper portion has a thread which is steeper than that of the lower portion whereby, when the lower portion is configured to be engaged in the bone and the upper portion is configured to be engaged in the threaded hole, rotation of the screw configured to move the screw into the bone is also configured to result in movement of the securing member away from the bone.

6. A system according to claim 5 wherein each of said two screws has a pitch ratio which is the ratio between the pitch angles of its upper and lower portions, and a length, and wherein the pitch ratios and/or the lengths are different between the two screws such that tightening of the two screws results in different lift distances of the support plate at the positions of the two screws.

7. A system according to claim 1 wherein one of the screw holes is non-threaded and the system comprises a further screw having a single constant pitch arranged to extend through the non-threaded hole to fix the securing member to the bone.

8. A system according to claim 1 wherein a further one of the screw holes is threaded and the system comprises a further screw having a single constant pitch arranged to extend through said further one of the screw holes to fix the securing member to the bone.

* * * * *